United States Patent [19]
Anderson et al.

[11] 4,112,117
[45] Sep. 5, 1978

[54] ALPHA-CYANO-O-ANISIDINO DERIVATIVES

[75] Inventors: Paul L. Anderson, Dover; Thomas F. Oglia, Parsippany, both of N.J.

[73] Assignee: Sandoz, Inc., E. Hanover, N.J.

[21] Appl. No.: 735,376

[22] Filed: Oct. 26, 1976

[51] Int. Cl.$^2$ .................. A61K 31/275; C07C 121/78
[52] U.S. Cl. .............................. 424/304; 260/465 D; 260/562 A
[58] Field of Search .................... 260/465 D; 424/304

[56] References Cited
PUBLICATIONS

Jacobs et al., J. Am. Chem. Soc., vol. 39, pp. 2188–2224 (pp. 2188–2190 + 2222 relied on) (1917).
Davis et al., Chemical Abstracts, vol. 50, 1654 (1956).
Kuliev et al., Chemical Abstracts, vol. 77, 151594n (1972).

*Primary Examiner*—Dolph H. Torrence
*Attorney, Agent, or Firm*—Gerald D. Sharkin; Richard E. Vila; Frederick H. Weinfeldt

[57] ABSTRACT

Alpha-cyano-o-anisidino derivatives, e.g., alpha-cyano-o-acetanisidide, are useful as hypolipidemic agents. The compounds are obtainable by reacting an appropriate 2-amidophenol with a haloalkylnitrile.

14 Claims, No Drawings

ALPHA-CYANO-O-ANISIDINO DERIVATIVES

This invention relates to o-anisidino compounds and more particularly to alpha-cyano-o-anisidino derivatives, to their use as pharmaceutical agents and to pharmaceutical compositions containing such compounds.

The compounds of this invention may conveniently be represented by the formula (I):

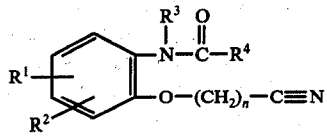

wherein
$R^1$ is a hydrogen atom, halogen having an atomic weight of from about 18 to 36, i.e. fluoro or chloro, trifluoromethyl ($CF_3$), nitro ($NO_2$), alkyl having from 1 to 4 carbon atoms, e.g., methyl or t-butyl, or alkoxy having from 1 to 4 carbon atoms, e.g., methoxy;

$R^2$ is a hydrogen atom, halogen having an atomic weight of from about 18 to 36, alkyl having from 1 to 4 carbon atoms or alkoxy having from 1 to 4 carbon atoms;

$R^3$ is a hydrogen atom or alkyl having from 1 to 3 carbon atoms;

$R^4$ is alkyl having from 1 to 6 carbon atoms, e.g., methyl or t-butyl; and $n$ is 1 or 2, provided that when $R^1$ is any of $CF_3$, $NO_2$ or a branched alkyl or branched alkoxy, and $R^2$ is located on a carbon atom adjacent thereto, then $R^2$ is not a branched alkyl or branched alkoxy.

Compounds I may conveniently be prepared by reacting an appropriate 2-amidophenol, i.e., a compound II:

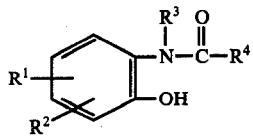

wherein $R^1$, $R^2$, $R^3$ and $R^4$ are as defined above, with an ω-haloalkylnitrile of formula III:

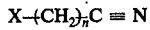

$$X\text{-}(CH_2)_n C \equiv N \qquad III$$

wherein $n$ is as defined above; and X is a halogen having an atomic weight of from about 34 to 127, i.e., chloro, bromo or iodo, i.e., process a).

The above-described process a) is carried out in the presence of a base, eg. potassium or sodium carbonate under essentially anhydrous conditions, in the presence of an inert organic solvent, e.g., a lower ketone such as acetone, with heating, e.g., at from about 60° to 120° C., preferably at the reflux temperature of the reaction mixture. Neither the temperature nor the particular solvent is critical.

The products of the above-described reaction are recovered, and refined where desired, in conventional manner, e.g., by crystallization, distillation or chromatographic techniques, such as thin layer or column chromatography.

Starting materials and reagents used in the above-described reaction, e.g., compounds II and III, are either known and obtained by methods described in the literature, or where not known, may be obtained by methods analogous to those described in the literature; some being commercially available.

Contemplated subclasses of compounds I include those where $R^1$ and $R^2$ are represented by substituents, as defined above, where: $R^1$ and $R^2$, respectively, are:
(a) $R^{1'}$ and/or $R^{2'}$ = H, halogen or alkyl or alkoxy as defined above; or $R^{1'}$ can additionally be $CF_3$;
(b) $R^{1''}$ and/or $R^{2''}$ = H, halogen or alkyl or alkoxy as defined above;
(c) $R^{1'''}$ and/or $R^{2'''}$ = H, or alkyl or alkoxy as defined above.

Further contemplated subclasses are those wherein $R^1$ = H and $R^2$ is any of $R^{2'}$, $R^{2''}$ or $R^{2'''}$ as defined above.

Further subclasses of compounds I are those wherein $(a^1)R^3$ is H; $(b^1)R^4$ is methyl and $(c^1)n = 1$; each of $R^1$ and $R^2$ being as defined above or as any of subclasses (a), (b) or (c); particularly where $R^3$ = H, and $n = 1$ and more particularly where $R^3$ = H, $n = 1$, $R^1$ = H and $R^2 = R^{2'''}$ (i.e. of type c), especially where $R^1 = R^2 = $ H.

UTILITY STATEMENT

The compounds of formula I are useful because they possess pharmacological activity in animals. In particular, the compounds are useful as hypolipidemic agents in the treatment of lipidemia as indicated by the fall in cholesterol and/or triglyceride levels in male albino Wistar rats weighting 110–130 g. initially. The rats are maintained on drug-free laboratory chow diet for seven days and then divided into groups of 6 to 10 animals. Each group, with the exception of the control, is then given orally 10 to 250 milligrams per kilogram of body weight per diem of the test compound for 6 days. At the end of this period, the animals are anesthetized with sodium hexobarbital and bled from the carotid arteries. Serum or plasma samples are collected and 1.0 ml. of the serum is added to 9.0 ml redistilled isopropanol. Two Auto-Analyzer cupsfuls of a mixture of zeolite-copper hydroxide and Lloyds reagent (Kessler, G., and Lederer, H., 1965, Technicon Symposium, Mediad Inc., New York, 345–347) are added and the mixture is shaken for 1 hour. Cholesterol and triglyceride levels are determined simultaneously on the same sample by Technicon N 24A (cholesterol) and N-78 (triglyceride) methodology. The mean total serum cholesterol levels are then computed and the hypocholesterol activity is expressed as the fall in cholesterol levels as a percentage of the control level. The change in serum triglyceride levels induced by the drug is computed as a percentage of the control triglyceride levels.

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The hypolipidemic effective dosage of active ingredient employed for the treatment of lipidemia may vary depending on the particular compound employed, the mode of administration and the severity of the condition being treated. However, in general, satisfactory results are obtained when the compounds of formula I are administered at a daily dosage of from about 4 milligrams to about 250 milligrams per kilogram of animal body weight, preferably given in divided doses two to four times a day, or in sustained release form. For most large mammals, the total daily dosage is from about 300 milligrams to about 3,000 milligrams. Dosage forms suitable for internal use comprise from about 75 to 1500 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired.

In the following examples, which are illustrative of the invention, temperatures are in degrees centigrade, and room temperature is 20 to 30° C., unless indicated otherwise.

EXAMPLE 1

α-Cyano-o-acetanisidide

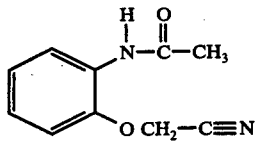

To a solution of 30 grams of 2-acetamidophenol (0.198 mole) in 500 ml. acetone is added 27.4 grams of potassium carbonate (0.198 mole). To the resulting suspension is added 16 grams of chloroacetonitrile (0.198 mole). The suspension is stirred for 18 hours at reflux. The reaction mixture is then filtered and the solvent removed under reduced pressure to yield a dark solid. Recrystallization from methylene chloride and petroleum ether (1:1) yields α-cyano-o-acetanisidide, mp, 115°–120° C.

EXAMPLE 2

5'-chloro-2'-(cyanomethoxy) Acetanilide

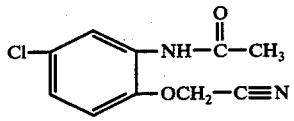

Step A, 4-chloro-2-acetamidophenol

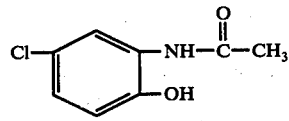

To a solution of 100 grams of 2 amino-4-chlorophenol (0.70 mole) in 1 liter of tetrahydrofuran is added 71 grams of triethylamine (0.70 mole). The resulting solution is cooled with an ice bath. To the solution is then slowly added 55 grams of acetyl chloride (0.70 mole) in 200 ml. of tetrahydrofuran. A precipitate forms (triethylamine hydrochloride). The solution is then filtered and the filtrate evaporated under reduced pressure, yielding a dark solid residue. Recrystallization of the residue from methylene chloride and petroleum ether (1:1) yields 4-chloro-2-acetamidophenol.

Step B, 5'-chloro-2'-(cyanomethoxy) acetanilide

To a solution of 25.0 grams of 4-chloro 2-acetamidophenol (0.135 mole) in 500 ml of acetone is added 18.7 grams of potassium carbonate (0.135 mole). To the resulting suspension is added 10.20 grams of chloroacetonitrile (0.135 mole). The suspension is stirred for 48 hours at reflux. The reaction mixture is then filtered and the solvent removed under reduced pressure to yield a dark solid residue. Recrystallization of the residue from methylene chloride-petroleum ether (1:1) followed by recrystallization twice more from methanol yields refined 5'-chloro 2'-(cyanomethoxy) acetanilide mp; 146°–149° C.

Repeating the procedure of this example, but using in place of the acetylchloride used in Step A, an approximately equivalent amount of n-propionyl chloride, there is accordingly obtained (a) 5'-chloro-2'-(cyanomethoxy) propionanilide (or 5'-chloro-2'-(cyanomethoxy)propionylaniline).

EXAMPLE 3

Capsules and tablets containing the ingredients indicated below may be prepared by conventional techniques and are useful in treating lipidemia, particularly hyperlipoproteinemia, in mammals at a dose of one capsule or tablet two to four times per day:

| Ingredient | Weight in Milligrams | |
|---|---|---|
| | Tablet | Capsule |
| α-cyano-o-acetanisidide | 150 | 150 |
| Tragacanth | 10 | |
| Lactose | 97.5 | 100 |
| Corn Starch | 25 | |
| Talcum | 15 | |
| Magnesium Stearate | 2.5 | |

EXAMPLE 4

Repeating the procedure of Example 1, but using in place of the chloroacetonitrile used therein, an approximately equivalent amount of β-chloropropionitrile, there is accordingly obtained o-(cyanoethoxy)acetanilide.

EXAMPLE 5

Following the procedures of Examples 1, 2 or 4 and employing appropriate starting materials and reagents there are similarly obtained:

(a) 4',5'-dichloro-2'-(cyanomethoxy)acetanilide;
(b) 5'-methoxy-2'-(cyanomethoxy)acetanilide;
(c) 5'-trifluoromethyl-2'-(cyanomethoxy)acetanilide,
(d) 3'-methyl-2'-(cyanomethoxy)acetanilide.
(e) o-(cyanoethoxy)propionanilide;
(f) 2'-(cyanomethoxy)2,2-dimethylpropionanilide (or o-cyanomethoxy)t-butyrylaniline);
(g) 5'-chloro-2'-(cyanoethoxy)acetanilide.
(h) o-(cyanomethoxy)n-propionanilide.
(i) N-methyl α-cyano-o-acetanisidide.

What is claimed is:
1. A compound of the formula

$$\begin{array}{c} R^3 \ O \\ | \ \| \\ R^1 \!-\!\!\bigcirc\!\!-\!\! N\!-\!C\!-\!R^4 \\ R^2 \quad O\!-\!(CH_2)_n\!-\!C\!\equiv\!N \end{array}$$

wherein
- $R^1$ is a hydrogen atom, halogen having an atomic weight of from about 18 to 36, $CF_3$, $NO_2$, alkyl having from 1 to 4 carbon atoms, or alkoxy having from 1 to 4 carbon atoms;
- $R^2$ is a hydrogen atom, halogen having an atomic weight of from about 18 to 36, alkyl having from 1 to 4 carbon atoms or alkoxy having from 1 to 4 carbon atoms;
- $R^3$ is a hydrogen atom or alkyl having from 1 to 3 carbon atoms;
- $R^4$ is alkyl having from 1 to 6 carbon atoms; and
- $n$ is 1;

provided that when $R^1$ is any of $CF_3$, $NO_2$ or a branched alkyl or branched alkoxy, and $R^2$ is located on a carbon atom adjacent thereto, then $R^2$ is not a branched alkyl or branched alkoxy.

2. A compound of claim 1 in which $R^3$ is a hydrogen atom.

3. A compound of claim 1 in which $R^4$ is methyl.

4. The compound of claim 3 which is alpha-cyano-o-acetanisidide.

5. The compound of claim 4 which is 5'-chloro-2'-(cyanomethoxy)acetanilide.

6. A compound of claim 1 in which $R^3$ is alkyl.

7. A pharmaceutical composition comprising a pharmaceutically-acceptable carrier and a compound of the formula $$\begin{array}{c} R^3 \ O \\ | \ \| \\ R^1 \!-\!\!\bigcirc\!\!-\!\! N\!-\!C\!-\!R^4 \\ R^2 \quad O\!-\!(CH_2)_n\!-\!C\!\equiv\!N \end{array}$$

wherein
- $R^1$ is a hydrogen atom, halogen having an atomic weight of from about 18 to 36, $CF_3$, $NO_2$, alkyl having from 1 to 4 carbon atoms, or alkoxy having from 1 to 4 carbon atoms;
- $R^2$ is a hydrogen atom, halogen having an atomic weight of from about 18 to 36, alkyl having from 1 to 4 carbon atoms or alkoxy having from 1 to 4 carbon atoms;
- $R^3$ is a hydrogen atom or alkyl having from 1 to 3 carbon atoms;
- $R^4$ is alkyl having from 1 to 6 carbon atoms; and
- $n$ is 1 or 2;

provided that when $R^1$ is any of $CF_3$, $NO_2$ or a branched alkyl or branched alkoxy, and $R^2$ is located on a carbon atom adjacent thereto, then $R^2$ is not a branched alkyl or branched alkoxy.

8. A composition of claim 7 in unit dosage form in which the compound is present in an amount of from about 75 to 1500 milligrams.

9. A composition of claim 8 in which the carrier is solid.

10. A composition of claim 7 in which the compound is alpha-cyano-o-acetanisidide.

11. A method of reducing the blood level of lipid materials in a mammal, comprising administering to said mammal an amount of a compound of the formula $$\begin{array}{c} R^3 \ O \\ | \ \| \\ R^1 \!-\!\!\bigcirc\!\!-\!\! N\!-\!C\!-\!R^4 \\ R^2 \quad O\!-\!(CH_2)_n\!-\!C\!\equiv\!N \end{array}$$

wherein
- $R^1$ is a hydrogen atom, halogen having an atomic weight of from about 18 to 36, $CF_3$, $NO_2$, alkyl having from 1 to 4 carbon atoms, or alkoxy having from 1 to 4 carbon atoms;
- $R^2$ is a hydrogen atom, halogen having an atomic weight of from about 18 to 36, alkyl having from 1 to 4 carbon atoms or alkoxy having from 1 to 4 carbon atoms;
- $R^3$ is a hydrogen atom or alkyl having from 1 to 3 carbon atoms;
- $R^4$ is alkyl having from 1 to 6 carbon atoms; and
- $n$ is 1 or 2;

provided that when $R^1$ is any of $CF_3$, $NO_2$ or a branched alkyl or branched alkoxy, and $R^2$ is located on a carbon atom adjacent thereto, then $R^2$ is not a branched alkyl or branched alkoxy; effective in reducing the blood level of lipid materials of said mammal.

12. A method of claim 11 in which the compound is administered in an amount of from about 300 to 3000 milligrams daily.

13. A method of claim 11 in which the mode of administration is oral.

14. A method of claim 11 in which the compound is alpha-cyano-o-acetanisidide.

* * * * *